United States Patent
Braunwarth et al.

(10) Patent No.: US 6,624,418 B1
(45) Date of Patent: Sep. 23, 2003

(54) OPTICAL TRANSMITTING AND RECEIVING DEVICE

(75) Inventors: Hubert Braunwarth, Friedberg (DE); Johann Florian, Schrobenhausen (DE); Günter Reisacher, Ingolstadt (DE)

(73) Assignee: Conti Temic microelectronic GmbH, Nürnberg (DE)

( * ) Notice: Subject to any disclaimer, the term of this patent is extended or adjusted under 35 U.S.C. 154(b) by 0 days.

(21) Appl. No.: 09/367,074

(22) PCT Filed: Feb. 3, 1998

(86) PCT No.: PCT/EP98/00554
§ 371 (c)(1),
(2), (4) Date: Feb. 1, 2000

(87) PCT Pub. No.: WO98/35221
PCT Pub. Date: Aug. 13, 1998

(30) Foreign Application Priority Data

Feb. 8, 1997 (DE) .......................... 197 04 793

(51) Int. Cl.[7] ............................................. G01N 21/00
(52) U.S. Cl. ................................. 250/341.1; 250/341.8
(58) Field of Search ..................... 250/341.1, 341.8, 250/339.01, 339.06, 339.11

(56) References Cited

U.S. PATENT DOCUMENTS 4,931,767 A * 6/1990 Albrecht et al. .......... 340/425.5
5,097,129 A  3/1992 De Vries et al.

FOREIGN PATENT DOCUMENTS

| DE | 19620147 | 12/1996 |
| EP | 0112498 A2 | 7/1984 |
| EP | 0122609 A1 | 10/1984 |
| EP | 0312788 A2 | 4/1989 |
| WO | WO 95/35493 | 12/1995 |

OTHER PUBLICATIONS

Halbleiter–Schaltungstechnik, U. Tietze, Ch. Schenk, 10. Auflage, Springer–Verlag Berlin 1993; Kap. 6.5; pp. 109–110.

* cited by examiner

Primary Examiner—Constantine Hannaher
Assistant Examiner—Timothy Moran
(74) Attorney, Agent, or Firm—Venable; Norman N. Kunitz

(57) ABSTRACT

An optical transmitting and receiving device with light-conducting receiver, which are arranged inside the housing, in front of a light-permeable cover between a transmitting unit and a receiving unit, so that the share of light reflected at the light-permeable cover of the transmitting unit is conducted to the receiving unit, thus making it possible to detect the operational readiness of the transmitting unit as well as the degree of soiling of the light-permeable cover.

5 Claims, 3 Drawing Sheets under conditions of the useful beam, i.e., the share of light reflected on the outside of the light-permeable cover, does not have to be changed, which further increases the operational reliability of the optical transmitting and receiving device.

OPTICAL TRANSMITTING AND RECEIVING DEVICE

BACKGROUND OF THE INVENTION

The invention relates to an optical transmitting and receiving device, e.g. as follows from European Patents EP 0 312 788 A2, EP 0 112 498 A2, EP 0 122 609 A1 or German Patent 196 20 147 A1.

In addition to its use for the transmission of digital data, optical transmitting and receiving devices are also used, for example, in analog applications for scanning spaces and structures, as light barriers, for measuring distances or detecting the number of seats occupied in motor vehicles. In the process, light is preferably used in the invisible wavelength range, particularly infrared light. Normally, the transmitting and receiving devices are protected against environmental influences by a housing, which is designed to be permeable to light in the corresponding wavelength range, at least in the area of the transmitting and receiving devices. The problem generally occurs that the light-permeable covers become dirty and the light yield is thus reduced.

On the one hand, the receiving signal levels depend on the distance to the reflecting surface and its remission. Thus, a low or missing receiving signal can be traced back to poor reflection at the surfaces outside of the transmitting and receiving device. On the other hand, it can also point to a defect in the transmitting device. The current-flow control for checking the failure of the transmitting device furthermore is not absolutely reliable.

Solutions that call for an increase in the transmitting output to compensate for the lowering of the receiving level due to dirty conditions must be evaluated especially critically. Thus, a considerable transmitting output is already required for scanning longer distances in the clean condition. If the output is increased further, damage to people in the scanned region cannot be ruled out completely over the long term. This should be avoided, particularly for the use of optical transmitting and receiving devices in the head region of people, as is standard practice for detecting the number of seats occupied.

The German Unexamined Published Patent Application 196 20 147 A1 discloses a device for measuring the line of sight, for which a share of the transmitted light is conducted outside of the light-permeable cover via glass fiber to a receiving device for a comparison evaluation. The soiled cover initially damps the reference beam, generated in this way, in the same way as the actual useful beam. To be sure, in the receiving device the reference beam can be used in a suitable manner for the comparison to the useful beam that is reflected in the observation area, so as to obtain information on the observation area according to the problem definition. However, this only takes into consideration the soiling through a weakening that is identical for both beams, but does not and is not intended to represent in particular a determination of the soiling. A quasi also error-encumbered variable is purposely used for the comparison (see lines 35–39 in column 2).

The European Patent 0 312 788 A2 shows a device for measuring the line of sight by means of a transmitting and receiving unit located inside the motor vehicle cab, where the windshield can be interpreted to be a light-permeable cover that is subjected to soiling. A low share of the light that is diffuse reflected at the windshield travels to the receiving unit, where it can be distinguished from the light shares reflected on the outside of the windshield and can be evaluated owing to the different transit times. The disadvantage in this case is the extremely small share of light that is diffuse reflected at the windshield and actually travels back to the receiving unit. For that reason, the device can provide only a very inaccurate determination of the soiling.

The European Patent 0 112 498 A2 discloses an arrangement for the automatic cleaning of windows, in which a separate transmitting and receiving unit for measuring the degree of soiling is suggested in one embodiment, which is arranged at a different angle to the light-permeable cover. Thus, the arrangement does not affect the measuring result from the other transmitting and receiving unit, but leads to considerable additional expenditure. European Patents 0 112 498 and particularly 0 122 609 disclose another alternative for guiding the light share, reflected at the light-permeable cover of the transmitting unit, by means of light-wave conductors to the receiving unit.

However, a time-window related differentiating between reflections at the inside and at the outside of the light-permeable cover is required in this case, which is involved with respect to control technology. In addition, the expenditure is relatively high, owing to the light-wave conductor, and the share of light reflected at the light-permeable cover that can be detected by means of this light-wave conductor, is very low because of the small opening.

SUMMARY OF THE INVENTION

Thus, it is the object of the invention to present an optical transmitting and receiving device, which makes it possible to forego a time-window related differentiation between reflections on the inside and on the outside of the light-permeable cover. The object is furthermore to increase in a simple manner the share of light reflected at the light-permeable cover, which can be detected.

These objects are solved with the characterizing features in patent claims 1 and 2. Advantageous modifications of the invention follow from the features in the dependent claims.

The light shares that are reflected unavoidably on the inside of the light-permeable cover and increase strongly with increased soiling can subsequently be conducted by light-conducting means to a receiving unit. As a result, it is possible to evaluate this internally reflected light share. On the one hand, this light share strongly depends on the degree of soiling while, on the other hand, the arrangement, structure and color conditions outside of the transmitting and receiving device do not affect it.

In order to be able to omit a time-window related differentiation between reflections on the inside and on the outside of the light-permeable cover, light is emitted according to patent claim 1 by a specific transmitting unit, for which the share of light reflected on the light-permeable cover is conducted via the light-conducting means to a first group of receiving units, while a second group of receiving units detects only the share of light reflected on the outside of the light-permeable cover. Thus, a receiving unit can receive only the light reflected on the inside of the light-permeable cover or the reflections occurring on the outside of the light-permeable cover.

A particularly high share of the light reflected on the light-permeable cover can be conducted by means of two parallel reflection surfaces to the receiving unit, wherein these surfaces can be realized particularly easily.

The optical transmitting and receiving device according to the invention can be realized simply, but is nevertheless extremely effective. Owing to the error-free detection of the outside effect of the degree of soiling, the analog receiving level can be corrected on the one hand with a correction factor or, if a threshold value is exceeded, a cleaning of the light-permeable cover can be initiated. Thus, it is conceivable that a cleaning device is actuated or an indicator is actuated, which urges the user to clean the light-permeable cover. There is no danger to the health of persons in the transmitting range. An increase in the transmitting level is not required.

The ratio of diffuse reflected light with total soiling and with no soiling and thus the detection of the degree of soiling can be optimized in that the distance between light-permeable cover and the transmitting and receiving units parallel to the transmitting direction is accordingly adapted to the distance perpendicular to the transmitting direction between the transmitting and receiving units. This distance, in turn, is selected in dependence on the size and distance of the target region.

A numerical ratio of the distances between 4,5 and 6,0 is conceivable in this case, for which an optimum of the-ratio between reflected light with total soiling and no soiling is found.

The invention is explained in the following in further detail with the aid of exemplary embodiments and Figures.

BRIEF DESCRIPTION OF THE DRAWINGS

FIG. 1a also shows the beam path of the transmitting and receiving device (1), shown as enlarged detail in FIG. 1b, with its light-permeable cover (4) at a distance a2 parallel to the transmitting direction. The transmitting units ($S_1 \ldots S_n$) scan the target region (Z) outside of the transmitting and receiving device (1), at a distance a3. FIG. 1b shows as enlarged detail an optical transmitting and receiving device (1), comprising n transmitting units ($S_1 \ldots S_n$) and m receiving units ($E_1 \ldots E_m$) at a distance a1, perpendicular to the transmitting direction. A transmitting optic (2) is arranged in front of the transmitting units ($S_1 \ldots S_n$), which directs the transmitted light beams to the target region (Z) outside of the transmitting and receiving device (1). Accordingly, a receiving optic (3) is arranged in front of the receiving units ($E_1 \ldots E_m$), which directs the reflected light beams from the target region (Z) to specific receiving units. A cover (4) is arranged in front of the transmitting and receiving device (1), at a distance a2 parallel to the transmitting direction. This cover protects the transmitting and receiving device (1) against soiling and environmental influences. The cover is permeable to light for the wavelength range of the transmitted light. It is unavoidable that a portion of the light transmitted by the transmitting units ($S_1 \ldots S_n$) is already diffuse reflected at the boundary surfaces on the inside the light permeable cover (4). The reflection surfaces (7a) and (7b) are arranged such that a portion of the diffuse reflected light can be separated out and conducted to the receiving side. There, it travels via the receiving optic (3) to specific receiving units. The reflection surfaces (7a, 7b), for example, can be designed as reflecting foils or vapor-deposited mirror surface.

Figure 1A:
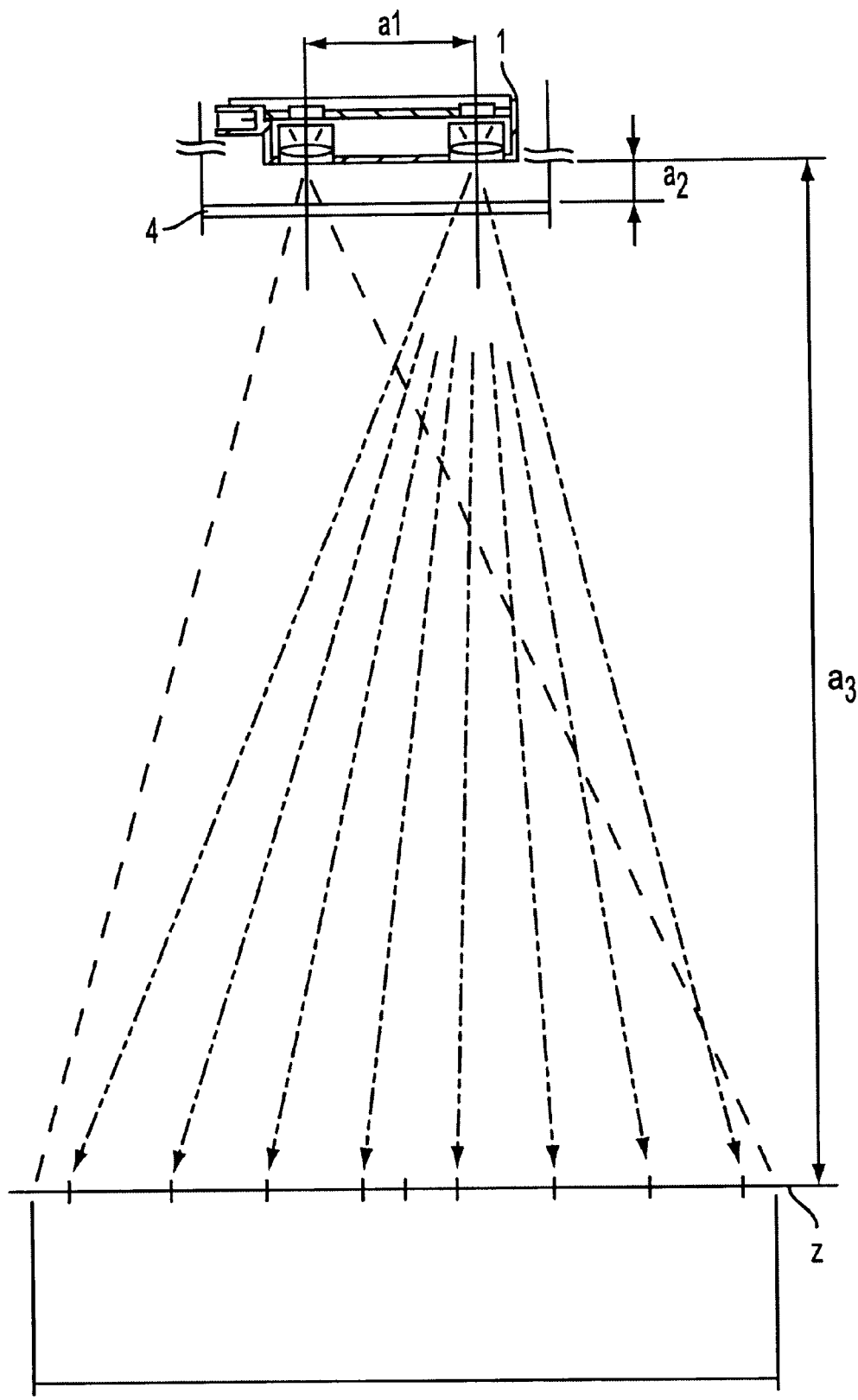
FIG. 1A shows a transmitting and receiving device according to the invention, as well as the beam path outside of this device into the target region.
Figure 1B:
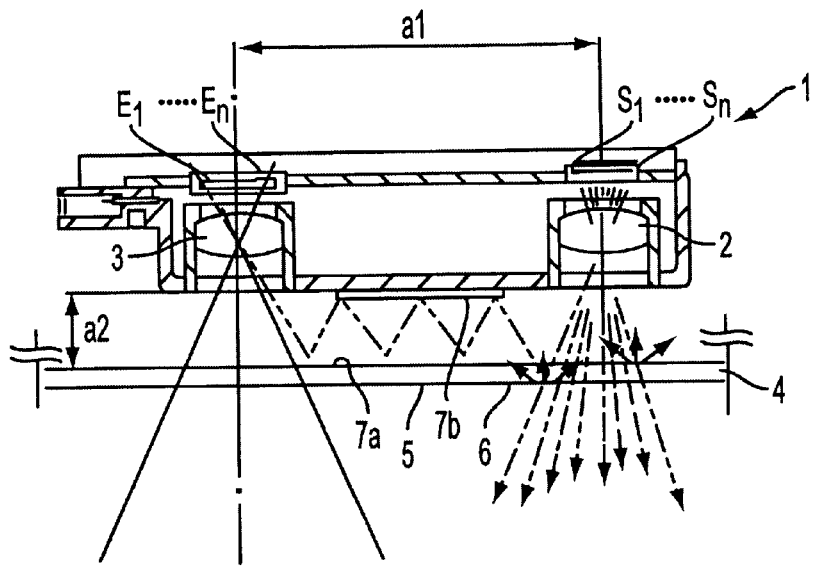
FIG. 1B is an enlarged detail from FIG. 1A of the transmitting and receiving device according to the invention, with light-conducting means inside of the light-permeable cover.
Figure 1C:
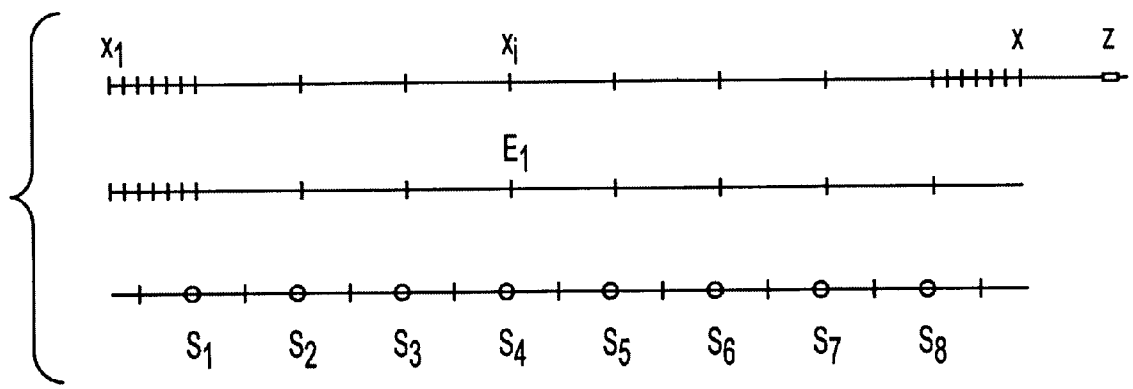
FIG. 1C is a cross-reference table for points in space assigned to specific transmitting and receiving units of the transmitting and receiving device in FIG. 1A or 1C.

In the process, spatial points $x_i$ in the target region (Z) can be assigned to the individual transmitting units, which points reflect the light transmitted by transmitting unit i (Si). The receiving units ($E_1 \ldots E_m$) are then arranged such that they detect the reflections from spatial points $x_i$. Thus, a transmitting and a receiving unit are coordinated with a spatial point $x_i$, as is shown visually in the cross-reference table in FIG. 1c.

Figure 2:
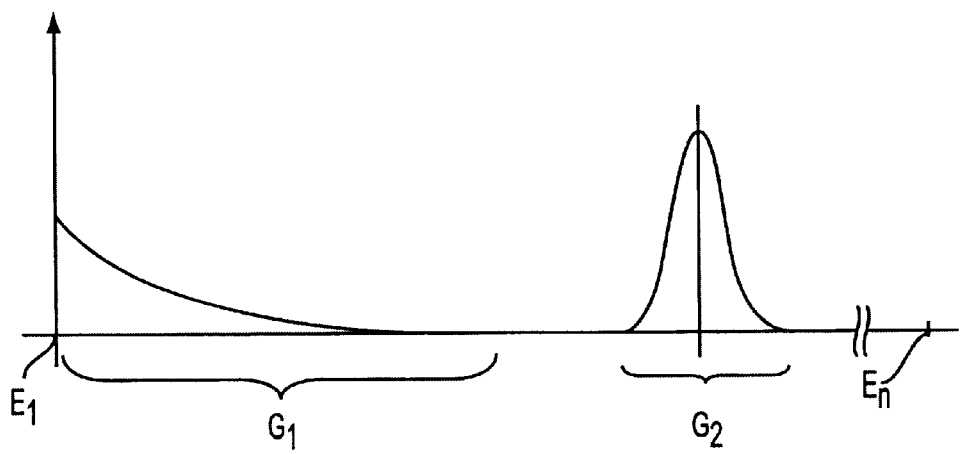
FIG. 2 shows receiving signals of the receiving units with useful signal range and soiling signal range.

FIG. 2 shows the receiving signals from the receiving units, following a transmitting pulse from transmission unit n ($S_n$). The light reflected on the outside on the target region n ($S_n$) leads to a deflection of the level in the coordinated first group of receiving units ($G_1$), according to patent claim 2 or 4. At the same time, a portion of the light transmitted by transmitting unit n ($S_n$) is reflected at the boundary surfaces of the light-permeable cover and is conducted to the second group of receiving units ($G_2$). While the signal for the soiling at the second group ($G_2$) of receiving units increases with increasing soiling, the useful signal at the first group ($G_1$) drops. However, if the first transmitting unit ($S_1$) is triggered, the useful signal share will be in the region of the second group ($G_2$), as was described in patent claim 5. Thus, the receiving units have a multi-functional use and ensure a particularly powerful and simultaneously cost-effective scanning of a large target region. The arrangement described in patent claims 3 or 4 can be realized in the same way as this exemplary embodiment, in that individual transmitting and receiving units are selected accordingly.

Figure 3:
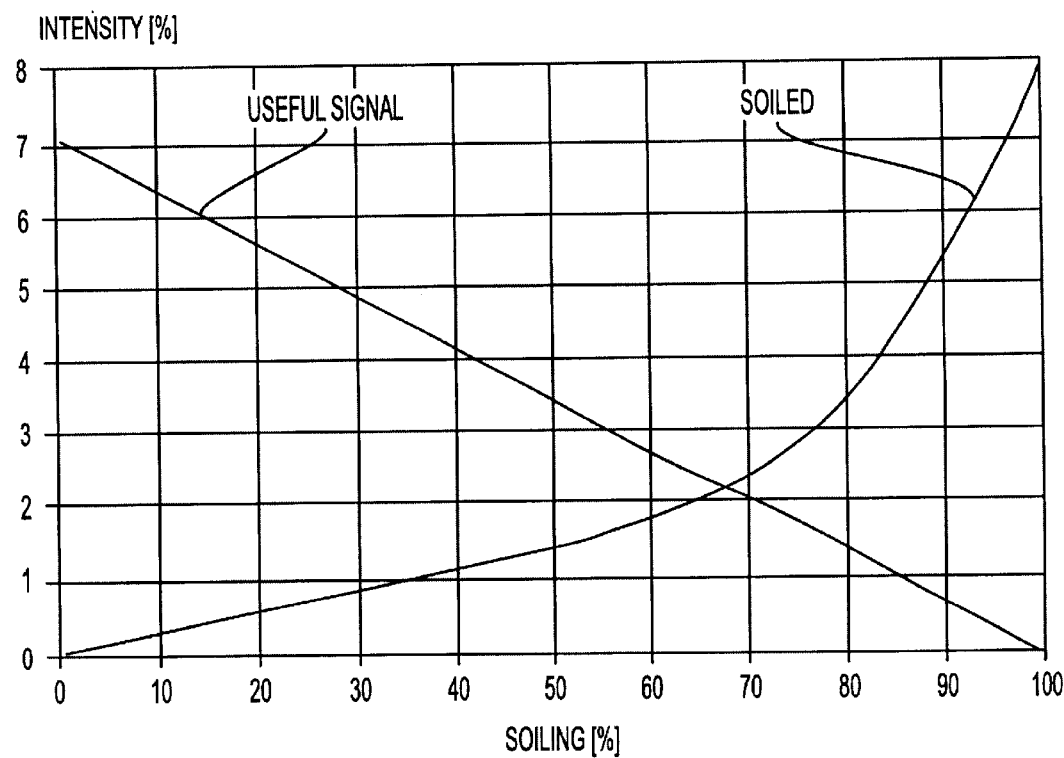
FIG. 3 shows the useful signal level and level of the received reflection within the light-permeable cover, in dependence on the degree of soiling.

FIG. 3 shows the change in the internally reflected light share and in the useful signal, reflected on the outside, in dependence on the degree of soiling. It can be seen clearly that the useful signal becomes weaker with increased soiling, while the share of light reflected inside the light-permeable cover increases. This can be detected through a change in the receiving signals and the comparison with the level for a new or cleaned cover. The received useful signal values can be corrected accordingly or, for example, a control light triggered if specific threshold values are exceeded. This control light urges the user to clean in the near future the cover over the optical transmitting and receiving device.

Figure 4:
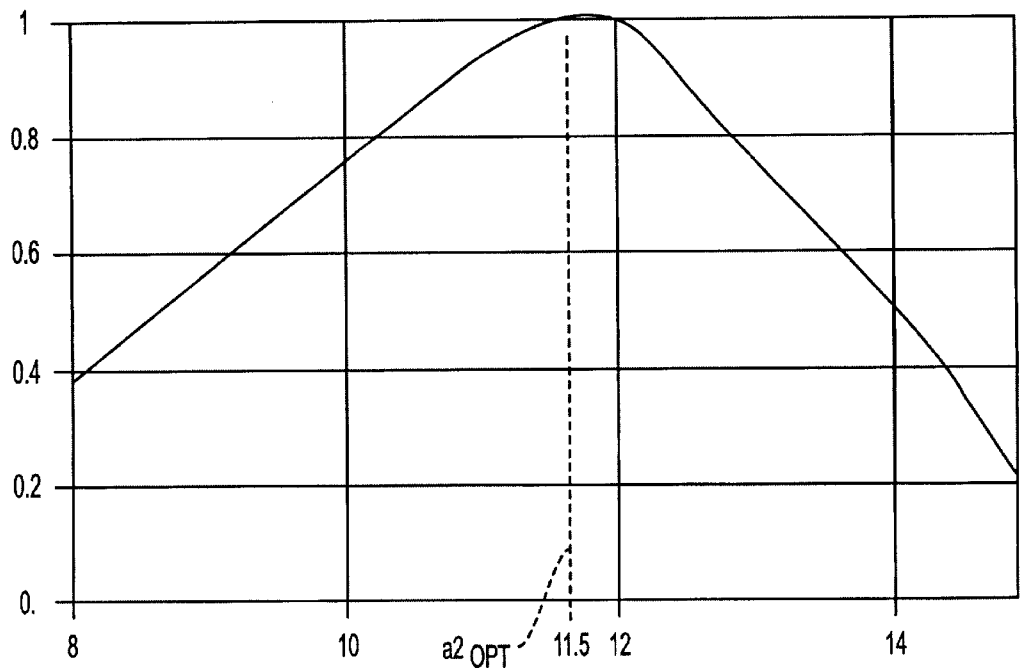
FIG. 4 shows the ratio of diffuse reflected light with total soiling and with no soiling, in dependence on the distance between light-permeable cover and transmitting and receiving units.

FIG. 4 shows the ratio of diffuse reflected light with total soiling and with no soiling in dependence on the distance a2 between light-permeable cover and at a predetermined distance between transmitting and receiving units. An optimum distance $a2_{opt}(4,5<a2_{opt}(\approx 5,2)<6,0)$ can be clearly seen, which thus best ensures the detection of the degree of soiling. By measuring the signal levels for two covers with different degree of soiling, this optimum distance $a2_{opt}$ can be found for any optimum distance a1 between the transmitting and receiving units by increasing the distance a2 from zero, but only until the ratio worsens again. An adaptation to the special features of the individual transmitting and receiving device is thus possible in a simple manner. If the reflected surfaces are brought together too closely, the light output transmitted by the internal, light-conducting means will decrease. If the distance surpasses the optimum, the light output arriving at the light-permeable cover becomes increasingly weaker and, in contrast, the unavoidable damping of the light-permeable cover becomes dominating, so that the light-permeable cover increasingly reflects the transmitting output.

What is claimed is:

1. An optical transmitting and receiving device (1), particularly in the infrared wave-band, comprising at least one transmitting unit (S) and at least one receiving unit (E), as well as a cover (4) that is light permeable at least in the region of the transmitting and receiving units (S, E), wherein the light emitted by the transmitting units is reflected outside of the cover and is received at the receiving units; light-conducting means are provided inside the cover (4), between the transmitting and receiving units (S, E), by means of which the share of transmitted light that is reflected at the light-permeable cover (4) of the transmitting unit is conducted to the receiving unit (E) for the purpose of evaluating the weakening of the light through soiling of the light-permeable cover (4); at least a first group and a second group (G1, G2) of receiving units (E) are provided; the first group (G1) of receiving units (E) is arranged such that it can receive only pulses that are transmitted by a specific transmitting unit (S) and reflected on the inside of the light-permeable cover, whereas the second group (G2) of receiving units (E) is arranged such that it receives only the reflections occurring outside of the light-permeable cover (4) of the pulses transmitted by the specific transmitting unit (S).

2. An optical transmitting and receiving device (1), in particular in the infrared wave-band, comprising at least one transmitting unit (S) and at least one receiving unit (E), having a cover (4) that is light-permeable at least in the region of the transmitting and receiving units (S, E), wherein the light emitted by the transmitting units is reflected outside of the cover and is received at the receiving units, wherein light-conducting means are provided inside the cover (4), between transmitting unit and receiving unit (S, E), by means of which the share of emitted light that is reflected on the light-permeable cover (4) of the transmitting unit is conducted to the receiving unit (E) for the purpose of evaluating the weakening of the light through soiling of the light-permeable cover (4), and wherein a first as well as a second mirror reflection surface (7a, 7b), arranged parallel thereto, is arranged as light-conducting means on the inside of cover (4), in the region between the transmitting unit (S1 . . . Sn) and the receiving unit (E1 . . . En).

3. An optical transmitting and receiving device according to claim 2, wherein with respect to a distance (a1), selected in dependence on the size and distance (a3) of the target region (Z), perpendicular to the transmitting direction between the transmitting and receiving units, the distance (a2) between the light-permeable cover and the transmitting or receiving units is selected parallel to the transmitting direction, such that it results in the highest ratio of diffuse reflected light with total soiling and with no soiling.

4. An optical transmitting and receiving device according to claim 3, wherein the numerical ratio of the distance (a1) perpendicular to the transmitting direction between the transmitting units and the receiving units to the distance (a2) between light-permeable cover and the transmitting or receiving units parallel to the transmitting direction ($a_1/a_2$) is between 4.5:1 and 6.0.

5. An optical transmitting and receiving device according to claim 4, wherein said numerical ratio is approximately 5.2.

* * * * *